United States Patent [19]
Lai

[11] Patent Number: 5,128,434
[45] Date of Patent: Jul. 7, 1992

[54] CONTROL OF HARD SEGMENT SIZE IN POLYURETHANE FORMATION

[75] Inventor: Yu-Chin Lai, Pittsford, N.Y.

[73] Assignee: Bausch & Lomb Incorporated, Rochester, N.Y.

[21] Appl. No.: 618,434

[22] Filed: Nov. 27, 1990

[51] Int. Cl.⁵ ............... C08G 18/10; C08G 18/32
[52] U.S. Cl. ............................ 528/65; 528/44; 528/48; 523/106; 351/160 R
[58] Field of Search ............... 525/100, 104, 123; 521/64, 89, 25; 528/26, 28, 75, 44, 48, 65; 523/106; 351/160 R

[56] References Cited

U.S. PATENT DOCUMENTS

| | | | |
|---|---|---|---|
| 2,976,576 | 3/1961 | Wichterle et al. | 18/58 |
| 3,220,960 | 11/1965 | Wichterle et al. | 521/89 |
| 3,428,043 | 2/1969 | Shepherd | 173/268 |
| 3,520,949 | 7/1970 | Shepherd et al. | 521/64 |
| 3,563,925 | 2/1971 | Kliment et al. | 521/109.1 |
| 3,566,874 | 5/1974 | Mitsch et al. | 424/81 |
| 3,607,848 | 9/1971 | Stoy et al. | 524/561 |
| 3,618,231 | 11/1971 | Nason | 35/35 |
| 3,679,504 | 7/1972 | Wichterle et al. | 156/62 |
| 3,810,874 | 3/1971 | Shepherd et al. | 128/349 |
| 4,143,017 | 3/1979 | Tarumi et al. | 523/106 |
| 4,752,627 | 6/1988 | Froix | 523/106 |
| 4,871,785 | 10/1989 | Froix | 523/106 |
| 5,034,461 | 7/1991 | Lai et al. | 525/100 |

OTHER PUBLICATIONS

"Urethane Polymer", Ency. Chem. Tech., vol. 23, pp. 576–606 (Wiley Intersciences 1983), H. Ulrich.

"Thermoplastic Elastomer", Ency. Chem. Tech., vol. 8, pp. 626-et seq. (Wiley Intersciences 1979), A. Finelli et al.

*Primary Examiner*—John Kight, III
*Assistant Examiner*—Duc Truong
*Attorney, Agent, or Firm*—Craig E. Larson; Denis A. Polyn

[57] ABSTRACT

Improved methods for forming urethane elastomers and corresponding urethane prepolymers are disclosed wherein diisocyanate and a low molecular weight diol are simultaneously mixed and reacted to form a hard segment which is subsequently reacted with a long chain diol to form the elastomer. Aliphatic diisocyanates are particularly desirable for the manufacture of contact lenses from the urethane prepolymers of this invention.

12 Claims, No Drawings

CONTROL OF HARD SEGMENT SIZE IN POLYURETHANE FORMATION

BACKGROUND OF THE INVENTION

The present invention relates to urethane elastomers and methods for their preparation.

Polyurethane is a versatile class of polymers with a variety of applications because its properties can be tailored simply by varying the components from which it is constructed (the rigid diols, the flexible polyols, and the polyisocyanate). Ulrich, H., "Urethane Polymer", in *Ency. Chem. Tech.*, Vol. 23, pp. 576-606 (Wiley Intersciences) (1983). Polyurethanes are used as adhesives, coatings, elastomers, foams, and fibers.

Polyurethane elastomers can be either thermoplastic or thermosetting. All linear segmented urethane elastomers are thermoplastic with good tear strength, impact resistance and other excellent mechanical properties. Finelli, A., et al., "Thermoplastic Elastomer", in *Ency. Chem. Tech.*, Vol. 8, pp. 626 et seq. (Wiley Intersciences) (1979). These properties are due in part to the strong hydrogen bonding between the hard segments of neighboring chains. Normally the thermoplastic polyurethanes are prepared by first forming the isocyanate-capped prepolymer of a flexible polyetherdiol or polyesterdiol, followed by adding the chain extender, which is the short chain diol, to form the high molecular weight polyurethane. Alternatively, the thermoplastic elastomers can be constructed by mixing the ingredients all at once, but with somewhat less useful physical properties.

In the two-step process to form the urethane elastomer, the length of the hard segment is relatively uniform in size. But when it becomes necessary to construct the hard segment before forming the soft segment, it is important to control the mode of reaction to preserve the excellent properties of polyurethane such as tear strength and toughness. A more uniform hard segment size enhances the attractive forces, i.e., hydrogen bonding, resulting in improved properties.

One method to control the size of the hard segment is by using an aromatic diisocyanate with differential reactivity between the two isocyanate groups. A prominent example of such a compound is tolylene diisocyanate ("TDI"). This is possible because of electronic and steric effects. However, this approach is not possible when using aliphatic diisocyanates or aromatic diisocyanates wherein the isocyanate groups are attached to different aromatic rings.

SUMMARY OF THE INVENTION

It has now been found that control of the size of hard segments prepared from diisocyanates is dramatically improved by simultaneously mixing the diisocyanate and the short chain diol. This result is desirable when employing aliphatic diisocyanates and aromatic diisocyanates wherein the isocyanate groups are attached to different aromatic rings. It has also been found that lower reaction temperatures enhance the selectivity of the reaction to the desired product.

DETAILED DESCRIPTION OF THE INVENTION

This invention is concerned with preparing urethane elastomers by first reacting two mole equivalents of a diisocyanate with about one mole equivalent of a low molecular weight diol. If this diol is represented by the symbol G where • denotes a hydroxyl radical and G represents the rest of the diol compound, and if the diisocyanate functional compound is represented by •D• where • represents an isocyanate radical, this first reaction can be schematically represented as follows:

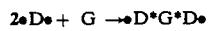

where * denotes a urethane or a ureido linkage. The first reaction produces a so-called "Hard" segment. As is known to those skilled in polymer chemistry, the product •D*G*D• is the mathematical average of all reaction product molecules. The reaction product of the actual reaction will contain •D• and •D(*G*D)$_c$*G*D with $c \geq 2$. Again, the formulas are numerical averages.

In the conventional method of urethane polymer preparation, 2 equivalents of diisocyanate is reacted with one equivalent of long chain polether diol or polyester diol to form a prepolymer with isocyanate endcaps. This prepolymer is then allowed to react with a short chain diol to form high molecular weight polymers. By this synthetic scheme, the hard segment, which is the reaction product of the short chain diol and the isocyanate groups in the prepolymer, is always uniform in size, i.e., it is exactly •D*G*D•, instead of a statistical distribution of sizes as •D(*G*D)$_c$•c=0,1,2,3, . . . as described in the preceding paragraph.

When it is desirable to prepare a urethane polymer or prepolymer by constructing the hard segment first because of special applications or reaction conditions required, the hard segment size is not uniform. In this scenario, the control of reaction conditions for hard segment formation is very critical in order to obtain hard segment with a narrow size distribution, which in turn, is very important to maintain the excellent mechanical properties of the urethane polymer. The control of reaction conditions to get the most favorable hard segment product is the subject of this invention.

It was found, as shown in the examples, that simultaneous mixing of reagents gave hard segments with the most favorable weight distribution (i.e., it has the highest content of •D*G*D•) while slow addition of short chain diol into a diisocyanate solution produced hard segments with less favorable size distribution. This phenomena is very prominent at high reaction temperature such as 80° C., and less when the reaction temperature is lower. The choice of solvent is irrelevant as long as the reagents are stable in the solvent employed.

Any diisocyanate with independent reactivities for the two isocyanate groups may be employed in the method of invention. These diisocyanate include any aliphatic diisocyanate and any aromatic diisocyanate with the isocyanate groups attached to different aromatic rings.

Thus, any diisocyanate (i.e., •D•) having independent reactivity may be employed in the method of this invention. "D" may be selected from the group consisting of alkyl, alkyl cycloalkyl, cycloalkyl, alkyl aromatic, and aromatic diradicals having 6 to 30 carbon atoms. Preferred aliphatic diisocyanates (i.e., •D•) are isophorone diisocyanate, hexamethylene-1,6-diisocyanate, biuret of hexamethylene-1,6-diisocyanate, and 4,4'-dicyclohexylmethane diisocyanate. The preferred aromatic diisocyanate is bis(4-isocyanatophenyl)methane.

Suitable low molecular weight diols (i.e., G ) include diols wherein G is selected from the group consisting of alkyl, cycloalkyl, alkyl cycloalkyl, aromatic, and alkylaromatic diradicals having 1 to 40 carbon atoms. The diols may have ether, thio, or amine linkages in the main chain. Particularly preferred low molecular weight diols are 2,2-(4,4' dihydroxydiphenyl)-propane (bisphenol-A), 4,4'-iso-propylidine dicyclohexanol (hydrogenated biphenol-A), ethoxylated bisphenol-A, propoxylated bisphenol-A, 2,2-(4,4'-dihydroxydiphenyl)-pentane, α,α'-(4,4'-dihydroxydiphenyl)-p-diisopropyl benzene, 1,3 cyclohexane diol, 1,4-cyclohexane diol-1,4-cyclohexane dimethanol, bicyclic and tricyclic diols such as 4,8-bis-(hydroxymethyl)-tricyclo [5.2.1.0$^{2,6}$]decane, neopentyl glycol, 1, 4 butanediol, 1,3-propanediol, 1,5-pentanediol, diethylene glycol, triethylene glycol and the like.

The product of the first reaction (between the diisocyanate and a low molecular weight idol) is reacted in a second stage with a long chain diol to form urethane elastomers. If A represents the long chain diol, the second reaction can be schematically represented as follows:

Suitable high molecular weight diols (i.e., A include diols wherein A is selected from the group consisting of alkyl, cycloalkyl, alkylcycloalkyl, aromatic, and alkylaromatic diradicals having molecular weights in excess of 400, preferably 1000-10,000, more preferably 2000-5000. Suitable diols also include fluorinated and silicone-containing analogs of the foregoing.

"A" preferably denotes a divalent polymeric radical chosen from the group of $$-(CH_2)_{n'}-O-(R^PO)_n-(CH_2)_{n''}-$$

$$-(CH_2)_{m'}-O-(R^FO)_m-(CH_2)_{m''}-$$

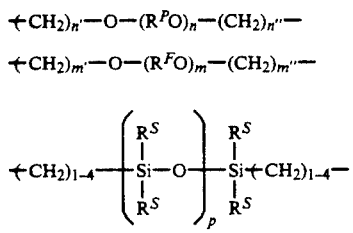

wherein
R$^P$ denotes a straight or branched alkyl group with 1 to 6 carbon atoms and n provides for a moiety weight of the radical between 2000 and 10,000;
R$^F$ denotes a fluorinated straight or branched alkyl radical with 1 to 6 carbon atoms and m provides a moiety weight of between 400 and 10,000;
R$^S$ denotes an alkyl radical or a short chain fluorinated alkyl radical with 1 to 3 carbon atoms; and p provides a moiety weight of 400 to 10,000;

Preferred high molecular weight diols include polymers of the following formulae

 a)

 b)

c)
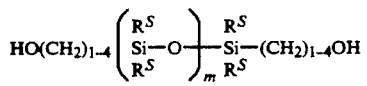

Formulae a) represents polyoxyalkyleneglycols which are generally commercially available in the molecular weight range called for in the present invention. These idols include polymers prepared from the epoxides: ethylene oxide 1,2-propylene oxide, 1,2-butylene oxide, 2,2 epoxydecane, 1,2-epoxyoctane, 2,3-epoxy norborane, 1,2-epoxy-3-ethoxy propane, 2,2-epoxy-3-phenoxypropane, 2,3-epoxypropyl-4-methoxy phenyl ether, tetrahydrofluran, 1,2-epoxy-3-cyclohexyloxy propane, oxetane, 1,2-epoxy-5-hexene, 1,2-epoxyethylbenzene, 1,2-epoxy-1-methoxy-2-methylpropane, benzyloxy propylene oxide, the like and combinations thereof.

The preferred polymers of this class are polypropylene glycols of molecular weights, 2000, 3000 and 4000 and more and polyoxyethylene polyoxypropylene block copolymers with molecular weight greater than 2000.

Formulae b) represents polyfluoroethers with α,ω-active hydrogens. This class of polymers can be synthesized as taught in U.S. Pat. No. 3,810,874. Generally, these polymers should have molecular weights between 400 and 10,000.

Formulae c) represents α,ω- dihydroxyl alkyl endblocked polysiloxane which for the purpose of the present invention should have a molecular weight in the range of 400 to 10,000. These polysiloxanes can be synthesized by reacting a disiloxane of the general formula

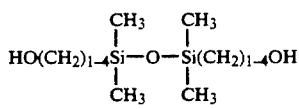

with cyclopolydimethyl siloxane under acidic conditions.

Alternately, the disiloxane can be replaced with dimethoxydimethylsilane or diethoxy dimethyl silane to produce the α,107 - dihydroxy endcapped polysiloxanes.

In general, each of the reaction stages is run until the reactive step is complete. Reaction progress may be monitored by acid base titration. The isocyanate content may be calculated by the difference of acid equivalents between a stock solution dibutylamine and its reaction product with the diisocyanate reaction intermediate. The reaction may also be monitored by ATR-IR for the appearance/disappearance of peaks at 1700 cm$^{-1}$, which indicated the presence of

and 2250 cm$^{-1}$ which indicated consumption of $-N=C=O$.

The synthesis of the prepolymer may be run neat or in solution. A wide range of aprotic solvents can be used to synthesize the prepolymers of the present invention. Solvents useful in the synthesis include toluene, methylene, chloride, benzene, cyclohexane, hexane, heptane and the like. Preferred solvents are toluene, methylene chloride and mixtures thereof.

Reaction of the precursors may be accomplished in the presence or absence of catalysts for urethane reactions, such catalysts being well known in the art. Among the suitable catalysts are tin salts and organic tin esters, such as dibutyl tin dilaurate, tertiary amines, such as triethyl diamine and other recognized catalysts, such as 1,4-diaza (2.2.2)-bicyclooctane (DABCO).

Preferably, the first step of elastomer synthesis in accordance with the present invention is carried out below about 100° C., most suitably within the range of from about 40° C. to about 80° C. Thereafter, the second step of the reaction is carried out at comparable temperatures, preferably within the range of from about 40° C. to 70° C. As will be apparent to those skilled in the art, optimal reaction conditions, such as temperatures and duration, are selected for each individual reaction system to achieve conditions that produce a favorable rate of reaction without fostering undesirable side reactions.

Optionally, the second stage can be run with molar excess of A to produce multiblock polymers of the general formula •(D*G*D*A)$_a$*D*G*D• where a is at least 1.

The urethane elastomers prepared as described above may be converted to prepolymers by the addition of a polymerizable end-capping agent in a third stage. In this stage, the reaction product from the second stage is reached with a molar excess of an end-capping monomer which has: 1) hydroxyl or amine functionality; and 2) some polymerizable unsaturation. If the endcapper is represented by the symbol E , where is —OH or —NH$_2$ or —NH—, the reaction proceeds generally as

[•D*G*D*]$_2$A + 2E → [E*D*G*D*]$_2$A

Suitable end-capping agents include polymerizable unsaturated organic radicals represented by the general chemical formula

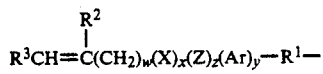

wherein
R$^1$ denotes a divalent alkylene radical with 1 to 10 carbon atoms;
R$^2$ denotes a —H or —CH$_3$ radical;
R$^3$ denotes a —H radical or an alkyl radical with 1 to 6 carbon atoms or a

radical where
Y is —O—, —S— or —NH— and R$^4$ denotes an alkyl radical with 1 to 12 carbon atoms;
X denotes

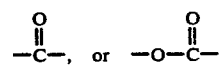

Ar denotes an aromatic radical with 6 to 30 carbon atoms;
a is at least 1;
w is 0 to 6;
x is 0 or 1;
y is 0 or 1; and
z is 1 or 1.

Specific examples are hydroxyethyl acrylate, hydroxyethyl methacrylate, aminoethyl methacrylate, 3 hydroxypropyl methacrylate, amino propyl methacrylate, hydroxyhexylacrylate, t-butylaminoethyl methacrylate, monoacrylate or monomethacrylate esters of bisphenol-A and/or bisphenol-B.

Prepolymer formation is typically effected at temperatures of from about room temperature to about 100° C., preferably from about 20° C. to about 40° C.

These prepolymers are especially useful in making biomedical materials due to this combination of physical strength and high oxygen permeability when copolymerized with state of the art ethylenically unsaturated biomedical monomers. The combination of advantageous properties is achieved due to the specific chemistry inherent in the claimed prepolymer.

The prepolymers upon polymerization form two domains which can be characterized as hard and soft domains, respectively. The soft domain generally have glass transition temperatures (Tg s) lower than room temperature whereas the hard domains have Tg s higher than room temperature. Upon polymerization, the hard segments of the prepolymer associate with one another and the soft segments form the soft domain which account for the oxygen permeability of the polymeric mass. The combination of hard and soft segments provides the polymer with superior mechanical properties otherwise unavailable.

These hard segments as mentioned before form hard domains in the final polymer or copolymer by association via hydrogen bonding with other rigid segments. The degree of association within the hard domain can be modified by controlling the amount of hydrogen bonding between the segments by either 1) decreasing the overall weight content of the hard segment in the prepolymer by increasing the molecular weight of the soft segment or 2) by decreasing the amount of hydrogen bonding density in the hard segment by either using relatively soft, longer chained diols, or by using primary amines or secondary amines capped low molecular weight compounds in conjunction with the diisocyanates rather than the diols.

The prepolymers of the present invention are particularly useful as comonomers with state of the art ethylenically reactive monomers useful in the field of biomedical materials. In general, these monomers are the hydroxyalkyl acrylates and diacrylates such as hydroxyethyl acrylate, hydroxypropyl acrylate, and the corresponding methacrylate compounds, including cyclohexyl methacrylate, methyl methacrylate, isobornyl methacrylate, lauryl methacrylate, triethylene glycol dimethacrylate, isobuty methacrylate and tetrahydrofurfuryl methacrylate and other unsaturated reactive monomers such as acrylamides, methacrylamides, pyrrolidinones, stryene and acrylonitrile can be used as well and other monomers known in the art including fluorinated analogs of all of the previously mentioned monomers and the organo silicone comonomers known in the art. Specific fluorocomonomers include:
(2,2,2-trifluoroethyl) itaconate
(hexafluoroisopropyl) itaconate
(1H, 1H-perfluorooctyl) itaconate
(1H, 1H, 111H-perfluoroundecyl) itaconate
(perfluoro-t butyl) itaconate
(pentafluorophenyl) itaconate
(2H, 2H-perfluorobenzyl) itaconate
(pentafluorophenylmethyl) itaconate
(decafluorocyclohexyl) itaconate
(1H-perfluorocyclohexyl) methyl itaconate
(1,1,1-trifluoroisopropyl) itaconate
1-methyl-4-(hexafluoroisopropyl) monoitaconate
4-(hexafluoroisopropyl) monoitaconate 1-(1H, 1H-perfluorooctyl)-4-hexafluoroisopropyl) itaconate
and methacrylate analogs thereof.

Specific organosilicon comonomers include:
tris(2-acetoxyethyldimethylsiloxy)silylpropyl acrylate and methacrylate
tris(2-carboxyethyldimethylsiloxy)silylpropyl acrylate and methacrylate
tris(3-hydroxypropyldimethylsiloxy)silylpropyl acrylate and methacrylate
acrylate and methacrylate functional, fluorosubstituted alkyl/aryl siloxanes such as:
tris(3,3,3 trifluoropropyl dimethylsiloxy) silyl propyl acrylate and methacrylate
tris[3-heptafluoroisopropoxy propyl)] dimethysiloxy silylpropyl acrylate and methacrylate
tris(pentafluorophenyl dimethysiloxy)silyl propyl acrylate and methacrylate.

Other potentially useful organosilicon comonomers include:
p-(pentamenthyldisiloxanyl) styrene
bis)trimethylsiloxy)
pyrrolidinonyldimethyl
siloxy-silylpropyl acrylate and methacrylate.

When used as comonomers these materials can be used from 5 to 85 weight percent of the final copolymer weight with the balance comprising the prepolymer portion.

Other di-ethylenically reactive monomers can also be used to effect the mechanical and surface properties. Such crosslinks are generally employed in the 0.1 to 5 wt % range.

The polymers and copolymers are formed by a free radical mechanism using a wide variety of known free radical catalysts such as the diacyl peroxides such as benzoyl peroxide; dialkyl peroxides such as di-tert, -butyl peroxide; ketone peroxides such as methylethyl ketone peroxide; and peresters which readily hydrolyze, e.g. tert-butyl peracetate, tert-butyl perbenzoate, di-tert-butyl diperphthalate, etc. A particularly useful class of peroxy initiators are the organic hydroperoxides such as cumene hydroperoxide, methylethyl ketone hydroperoxide, tert-butyl hydroperoxide, etc. The initiators should be used at a concentration of about 0.01 percent to about 10 percent by weight of the total formulation, preferably about 0.1 percent to about 5 percent by weight. Another useful class of initiators comprises carbonyl-containing ultraviolet-activated free radical generators, such as acetophenone, benzophenone, and the benzoin ethers. Other suitable UV initiators are known in the art. Initiator mixtures may also be used.

Solvents can be used in the final copolymerization and/or polymerization process. Solvent choice will depend upon the solubility parameters of the prepolymer and of the comonomers used, if any, and should be chosen to allow full solubilization of all polymerizate components.

In certain instances, the copolymerization process should be carried out without solvent. For instance, when 2-hydroxyethyl methacrylate (HEMA) is copolymerized with one of the prepolymers formed with polyethylene glycol, use of toluene causes the HEMA to form heterogenous domains which are not stable under aggressive hydrolytic conditions.

As mentioned, the prepolymers of the present invention are particularly useful in forming shaped articles used in biomedical applications. These polymers and copolymers can be used to make biomedical devices i.e. shaped articles, such as dialyzer diaphragms, to prepare artificial kidneys and other biomedical implants, such as disclosed in Wichterle, U.S. Pat. No. 2,976,576 and Wichterle, U.S. Pat. No. 3,220,960. The instant polymers and copolymers can be used in preparing therapeutic bandages as disclosed in Shephard, U.S. Pat. No. 3,428,043. The instant polymers and copolymers can also be used in preparing medical surgical devices e.g. heart valves, vessel substitutes, intra-uterine devices, membranes and other films, dialyzer diaphragms, catheters, mouth guards, denture liners and other such devices as disclosed in Shephard U.S. Pat. No. 3,520,949 and Shephard U.S. Pat. No. 3,618,231. The instant polymers and copolymers can be used to modify collagen to make blood vessels, urinary bladders and other such devices as disclosed in Kliment U.S. Pat No. 3,563,925. The instant polymers and copolymers can be used to make catheters as disclosed in Shephard U.S. Pat. No. 3,566,874. The instant polymers and copolymers can be used as semipermeable sheets for dialysis, artificial dentures and all of such disclosures as set forth in Stoy U.S. Pat. No. 3,607,848. The instant polymers and copolymers can be used in ophthalmic prostheses and all other uses disclosed in Wichterle U.S. Pat. No. 3,679,504. They may also be used as a polymeric matrix for controlled release of active pharmaceutical agents.

A preferred application for the urethane prepolymers of this invention is the manufacture of contact lenses. Because aromatic diisocyanates have been found to discolor contact lenses, aliphatic diisocyanates are preferred for this application.

Separation of the urethane elastomers and prepolymers of this invention from byproducts is difficult, if not impossible, because of the high reactivity of the materials. Accordingly, increased selectivity in the reactions leading to the desired elastomer/prepolymer product is essential. This is particularly so when prepolymers are incorporated in contact lens materials as is contemplated in particularly preferred embodiments of this invention.

The isophorone diisocyanate ("IPDI") used in the following examples was distilled under reduced pressure. Gas chromatographic analysis indicated that it was 72% cis and 28% trans. When diethylene glycol ("DEG") was used in the following examples with toluene as a reaction solvent, DEG (99%+ with less than 0.04% water as determined by the Karl-Fisher method) was azeotropically distilled with toluene prior to use. Otherwise, it was dried over 3A molecular sieves. Toluene was dried with sodium. Methylene chloride was dried by 3A molecular sieve, with resulting water content less than 0.01%.

EXAMPLES 1-4 and COMPARATIVE EXAMPLES A-D

IPDI solution (1 equivalent) in toluene or in methylene chloride, with dibutyltin dilaurate (1.1% of the weight of the reactants--IPDI and DEG) was added to a dry, three-necked flask under nitrogen blanket. The solution was heated at the specified temperature. Then the dry DEG solution (0.5 equivalent) was added over the period of time indicated. The contents were then heated and stirred under a nitrogen blanket until the isocyanate content was reduced one-half as determined by acid-base titration.

An aliquot was removed, reacted with excess butylamine and then vacuum stripped. The butylamine was added to form a stable urea for characterization purposes. When the isocyanate-capped adduct was not properly deactivated, it would pick up moisture, resulting in erroneously large molecular weight values.

The urethane-urea adduct was then analyzed by gel permeation chromatography for size distribution. Results are shown below in Table 1. In the Table, A represents urea-capped IPDI-(DEG-IPDI)n wherein n is no less than 2; B represents urea-capped IPDI-DEG-IPDI which is the desired product; and C represents urea-capped IPDI.

TABLE 1

| | Example | | | | | | | |
|---|---|---|---|---|---|---|---|---|
| | A | B | C | 1 | D | 2 | 3 | 4 |
| Temperature (°C.) | 100 | 80 | 80 | 80 | 50 | 50 | 50 | 25 |
| Solvent | | | toluene | | | | | $CH_2Cl_2$ |
| Mixing Time (hours) | 3 | 3 | 1.5 | 0 | 3 | 0 | 0 | 0 |
| Distribution of Products (weight %) | | | | | | | | |
| A | 31 | 37 | 25 | 21 | 25 | 22 | 21 | 30 |
| B | 42 | 35 | 41 | 55 | 52 | 59 | 57 | 56 |
| C | 27 | 28 | 33 | 24 | 23 | 19 | 20 | 14 |
| Ratio of B/A | 1.35 | 0.95 | 1.64 | 2.62 | 2.08 | 2.68 | 2.71 | 1.87 |

The data shows the effects of modes of addition and reaction temperature on the size distribution of hard segments. With toluene at 80° C., it was found that simultaneous mixing of DEG with IPDI gave the highest concentration (55%) of the end-capped DEG (IPDI-DEG-IPDI), while slow addition (3 hours) of DEG gave the lowest concentration (35%). Note that reaction at a lower temperature (50° C., as compared to the higher temperature of 80° C.) gave a higher concentration of the desired hard segment regardless of mode of addition. Simultaneous mixing of reagents gave superior results at all temperatures studied. Alternate solvents did not change the distribution of reaction products.

What is claimed is:

1. An improved method for forming a urethane elastomer wherein a diisocyanate selected from the group consisting of aliphatic diisocyanates and aromatic diisocyanates wherein the isocyanate groups are attached to different aromatic rings is reacted with a low molecular weight diol to form a hard segment which is subsequently reacted with a long chain diol, the improvement which comprises simultaneously mixing the diisocyanate and low molecular weight diol used to form the hard segment.

2. An improved method for forming a urethane prepolymer wherein:

(a) a diisocyanate selected from the group consisting of aliphatic diisocyanates and aromatic diisocyanates wherein the isocyanate groups are attached to different aromatic rings is reacted with a low molecular weight diol to form a hard segment,
   (b) the hard segment is reacted with a long chain diol to form a urethane elastomer,
   (c) and the elastomer is reacted with an end-capping agent having a polymerizable functionality;

the improvement which comprises simultaneously mixing the diisocyanate and the low molecular weight diol used to form the hard segment.

3. The methods of claims 1 or 2 wherein the diisocyanate is an aliphatic diisocyanate.

4. The methods of claim 3 wherein the aliphatic diisocyanate is selected from the group consisting of isophorone diisocyanate, hexamethylene-1,6-diisocyanate, biuret of hexamethylene-1,6-diisocyanate, and 4,4'-dicyclohexylmethane diisocyanate.

5. The methods of claim 3 wherein the aliphatic diisocyanate is isophorone diisocyanate.

6. The methods of claim 1 or 2 wherein the diisocyanate is bis(4-isocyanatophenyl)methane.

7. The methods of claim 1 or 2 wherein the diisocyanate and the low molecular weight diol are reacted at a temperature within the range of about 40° C. to about 80° C.

8. An improved urethane prepolymer prepared by a method wherein:

(a) a diisocyanate selected from the group consisting of aliphatic diisocyanates and aromatic diisocyanates wherein the isocyanate groups are attached to different aromatic rings is reacted with a low molecular weight diol to form a hard segment,
   (b) the hard segment is reacted with a long chain diol to form a urethane elastomer,
   (c) and the elastomer is reacted with an end-capping agent having a polymerizable functionality;

the improvement which comprises simultaneously mixing the diisocyanate and the low molecular weight diol used to form the hard segment.

9. A contact lens prepared from a monomer mixture comprising the urethane prepolymer of claim 8.

10. The contact lens of claim 9 wherein the prepolymer is prepared from an aliphatic diisocyanate.

11. The contact lens of claim 10 wherein the prepolymer is prepared by reacting the aliphatic diisocyanate and the low molecular weight diol are reacted at a temperature within the range of about 40° C. to about 80° C.

12. The contact lens of claim 11 wherein the aliphatic diisocyanate is isophorone diisocyanate.

* * * * *

UNITED STATES PATENT AND TRADEMARK OFFICE
CERTIFICATE OF CORRECTION

PATENT NO. : 5,128,434

DATED : July 7, 1992

INVENTOR(S) : Yu-Chin Lai

It is certified that error appears in the above-identified patent and that said Letters Patent is hereby corrected as shown below:

Column 2, line 1, insert --♦-- before "G", after "G", and after "where".

Column 2, line 7, insert --♦-- before "G" and after "G".

Column 3, line 1, insert --♦-- before "G" and after "G".

Column 3, line 21, insert --♦-- before "A" and after "A".

Column 3, line 25, insert --♦-- before "A" and after "A".

Column 3, line 27, insert --♦-- before "A" and after "A".

Column 4, line 39, replace "107" with --$\omega$--.

Column 5, line 16, insert --♦-- before "A" and after "A".

Col. 5, line 26, insert --♦--. after "E", and after "where".

Col. 5, line 64, change "1 or 1" to --0 or 1--.

UNITED STATES PATENT AND TRADEMARK OFFICE
CERTIFICATE OF CORRECTION

PATENT NO. : 5,128,434
DATED : July 7, 1992
INVENTOR(S) : Yu-Chin Lai

It is certified that error appears in the above-indentified patent and that said Letters Patent is hereby corrected as shown below:

Col. 7, line 21, change "pentamenthyldisiloxanyl" to --pentamethyldisiloxanyl--.

Signed and Sealed this

Fifth Day of October, 1993

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,128,434
DATED     : July 7, 1992
INVENTOR(S) : Yu-Chin Lai

It is certified that error appears in the above-identified patent and that said Letters Patent is hereby corrected as shown below:

Column 5, line 26, insert -- ◆ -- after "E", and after "where".

Signed and Sealed this

Eighth Day of March, 1994

Attest:

BRUCE LEHMAN

Attesting Officer    Commissioner of Patents and Trademarks